US005800813A

United States Patent [19]
Casas

[11] Patent Number: 5,800,813
[45] Date of Patent: Sep. 1, 1998

[54] TREATMENT OF CRYPTOSPORIDIUM INFECTIONS

[75] Inventor: Ivan A. Casas, Raleigh, N.C.

[73] Assignee: Biogaia Biologics AB, Stockholm, Sweden

[21] Appl. No.: 748,174

[22] Filed: Nov. 12, 1996

[51] Int. Cl.$^6$ .................................................. C12N 1/20
[52] U.S. Cl. ............................................... 424/93.45
[58] Field of Search ........................................ 424/93.45

[56] References Cited

U.S. PATENT DOCUMENTS 5,439,678  8/1995  Dobrogosz et al. ................ 924/93.45

OTHER PUBLICATIONS

Argenzio, The Pig as a Model for Studying the Pathobiology of Intestinal Transport . . . , Adv. Swind Biomed Res, Plenum, NY 1966.

Gomez et al., High Levels of Inorganic Sulfate Cause Diarrhea in Neonatal Piglets, J. Nutr. 125: 2325–2332, 1995.

Alak et al., FASEB Journal 10 (3): A796 (1996).

Alak et al., Gastroenterology 110 (4 Suppl.): A852 (1996).

*Primary Examiner*—Jean C. Witz
*Attorney, Agent, or Firm*—Lynn E. Barber

[57] ABSTRACT

A method of reducing symptoms associated with cryptosporidia infection in mammals including humans in which *L. reuteri* cells are administered to the mammal in an amount sufficient to reduce diarrhea in the animal to a normal level. Daily administration as soon as cryptosporidia infection symptom are observed optimizes results. The *L. reuteri* cells may also be administered prophylactically to a mammal before exposure to cryptosporidia. The cells may be administered suspended in a liquid or in dry form.

7 Claims, 1 Drawing Sheet

TREATMENT OF CRYPTOSPORIDIUM INFECTIONS

BACKGROUND OF THE INVENTION

1. Field of the Invention

This invention relates to methods of treating cryptosporidia-infected animals.

2. Description of the Related Art

Cryptosporidium infections in mammals, including humans, generally is caused by drinking of contaminated ground-water or ingestion of food made with contaminated ground-water. The original contamination source is primarily the feces of infected cattle. Cryptosporidium causes diarrhea which can be extremely serious or fatal in newborn or immunocompromised animals, for example, human beings with HIV or AIDS. Ongoing attempts to control cryptosporidia include trials of various chemicals to reduce infections and attempts to isolate epitopes and develop antibodies.

*Lactobacillus reuteri* has been found to be present in the gastrointestinal tract of humans and animals (Kandler et al., *Lactobacillus reuteri* sp. nov., a new species of heterofermentative Lactobacilli. Zbl. Bakt. Abt. Orig. Cl:264–269, 1980). This species has been shown to have antibacterial and antiviral activity.

A well-accepted model for determining the effect of a particular treatment on cryptosporidia infections in humans and to ascertain the effects of cryptosporidia infection and evaluate its diarrheal pathophysiology and therapy is the use of newborn piglets. For about a decade, use of piglets has enabled scientists to understand how intestinal electrolyte transport occurs, especially the regulation of the causes of diarrheal diseases. The pig model system is a better model system than the rodent system because the piglet obtains all of its passive immunity postnatally, and is thus initially agammaglogulinemic and easily infected with pathogens. Thus, early work showing bacterial enterotoxin action, such as that of *Escherichia coli*, was derived from studies using the pig model, as is our understanding of malabsorptive disease caused by rotaviruses (Argenzio, R. A., The pig as a model for studies of diarrhea pathophysiology, in *Swine as a Model for Biomedical Research*, M. Tumbelson, ed, Plenum Press, N.Y., pp. 441–452, 1986). More recently, studies by Argenzio and coworkers on cryptosporidia in piglets have helped elucidate the mechanisms altered transport which occurs in this acute diarrheal condition (See Gastroenterology 98:1129–1149, 1990; 104:440–447, 1993; and Gastroenterology 106:1418–1428, 1994).

The preferred method of utilizing artificially reared neonatal piglets as a model to evaluate the effect of various treatments on bowel function in humans, particularly human infants and immunocompromised humans, is the use of the "Autosow" manufactured by Sun Technologies, formerly Eutectic Electronics (Raleigh, N.C.). Other examples of use of the Autosow include studies of the causation of diarrhea by sulfate levels in water (Gomez et al., J. Nutr. 125:2325, 1995: the same sulfate level which caused pig diarrhea was that which had been seen to cause human infant diarrhea).

It is therefore an object of the invention to provide a method for treating mammals, including humans, to prevent or control cryptosporidia infections.

Other objects and advantages will be more fully apparent from the following disclosure and appended claims.

SUMMARY OF THE INVENTION

The invention herein is a method of reducing symptoms associated with cryptosporidia infection in mammals including humans in which *L. reuteri* cells are administered to the mammal in an amount sufficient to reduce diarrhea in the animal to a normal level. Daily administration as soon as cryptosporidia infection symptom are observed optimizes results. The *L. reuteri* cells may also be administered prophylactically to a mammal before exposure to cryptosporidia. The cells may be administered suspended in a liquid or in dry form.

Other objects and features of the inventions will be more fully apparent from the following disclosure and appended claims.

DETAILED DESCRIPTION OF THE INVENTION AND PREFERRED EMBODIMENTS THEREOF

Figure 1:
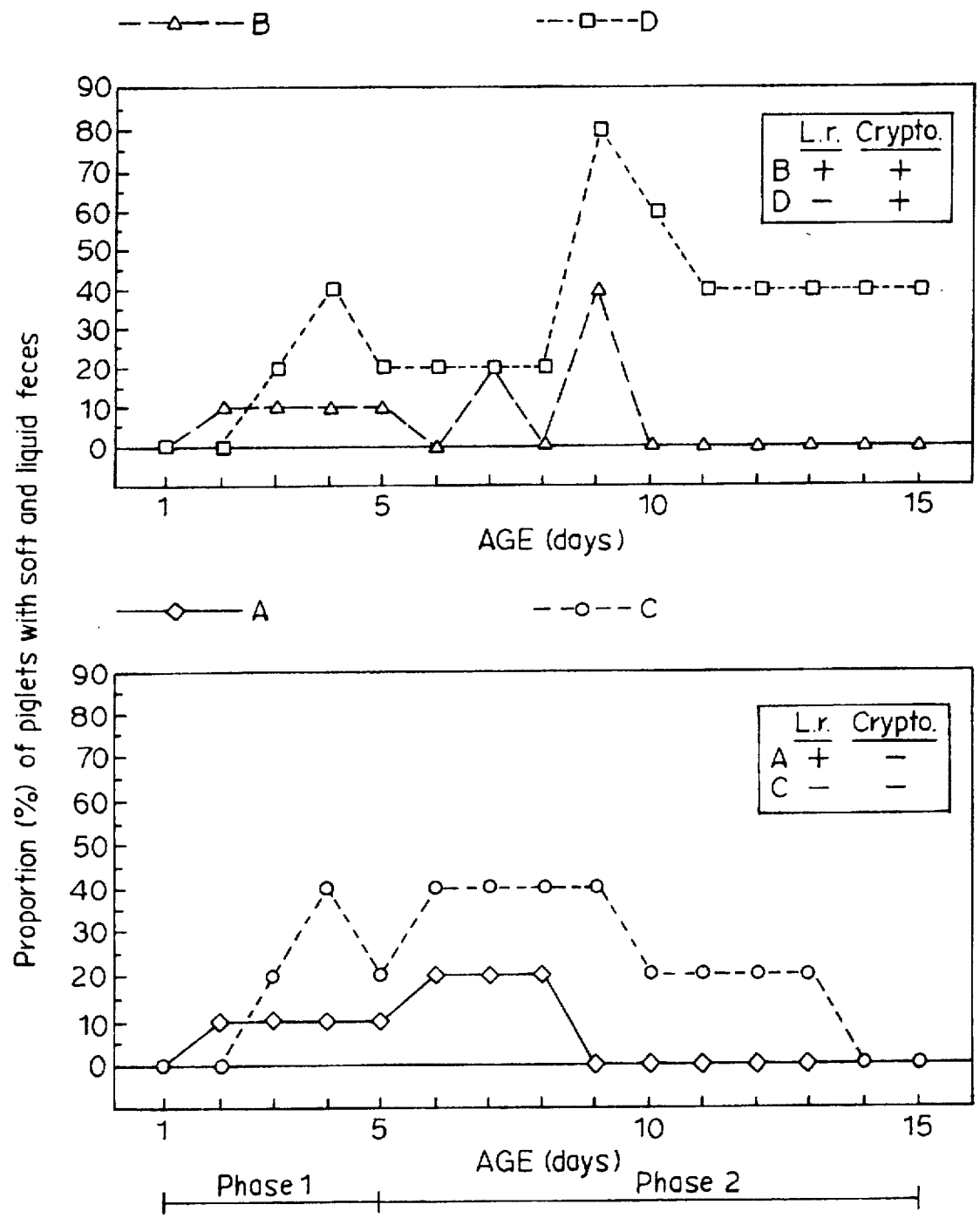
FIG. 1 shows two graphs. The upper graph of FIG. 1 shows the effect of *L. reuteri* on feces consistency in treatments B and D (plus cryptosporidia), and the lower graph shows the effect of *L. reuteri* on feces consistency in treatments A and C (no cryptosporidia).

The present invention provides a method of reducing diarrhea caused by Cryptosporidium infections in mammals, including humans.

The invention has been evaluated in the piglet model discussed above to determine the effect of *L. reuteri* on the rate of growth, feed intake, feces consistency and intestinal microbial population (total lactobacilli and *L. reuteri*) of non-infected and cryptosporidia-infected, artificially reared piglets through a 15-day experimental period. The study had two phases: (1) during the period between 1 and 5 days of piglets' age, when the effect of administration of *L. reuteri* was evaluated, and (2) during the period between 5 and 15 days of piglets' age, when the interaction between *L. reuteri* and cryptosporidia challenge was assessed.

The results discussed herein show that administration of *L. reuteri* to mammals which have been exposed to Cryptosporidium, particularly mammals without active immunity, reduces diarrheal symptoms.

The features and advantages of the present invention will be more clearly understood by reference to the following examples, which are not to be construed as limiting the invention.

EXAMPLES

Example I

There were two phases to the study. During phase 1 of the study (days 1–5 of the piglets' lives), the effect of administration of *L. reuteri* was evaluated. During phase 2 (5–15 days), the interaction between *L. reuteri* administration and cryptosporidia challenged was assessed. The experiment was performed in the facilities and under the supervision of Dr. Guillermo Gomez, Department of Animal Science, North Carolina State University, Raleigh, N.C.

Twenty newborn piglets, from two litters, were used. Piglets did not consume any sows' colostrum and were moved to an Autosow™ (Sun Technologies, Raleigh, N.C.) immediately after farrowing. Piglets were individually caged and fed the experimental diets at a rate of 300 ml per kilogram of body weight per day, in 16 feedings per day (every 1.5 hr feeding schedule). Piglets were randomly assigned to experimental groups according to liveweight, sex and litter origin.

During the first five days (phase 1), piglets were fed diets containing 20%, 15%, 10% and 0% cow's colostrum for the $1^{st}$, $2^{nd}$, $3^{rd}$ and $4^{th}/5^{th}$ day, respectively. Half of the piglets were fed these diets without *L. reuteri* (diet C) while the other half received diets supplemented with *L. reuteri* (diet A) at a final concentration of $1.1\times10^7$ and $2.3\times10^8$ colony forming units (CFU) per ml of diet. Data obtained during this period were statistically analyzed as a randomized complete block design with two treatments (plus *L. reuteri* and minus *L. reuteri*). The *L. reuteri* strain used was strain 1063 (ATCC No. 53608, which is available to the public at the American Type Culture Collection, Rockville, Md. having been deposited there under the Budapest Treaty Apr. 17, 1987), provided by Biogaia Biologics, Inc.

On day 5, half of the piglets fed the *L. reuteri*-supplemented diet as well as half of those fed the non-supplemented diet, were infected with a *Cryptosporidium parvum* preparation containing $1\times10^8$ oocysts per ml, in 10 ml of diet). On day 8, the same piglets were infected with the same dose.

From day 5 until the end of the experimental period (15 days of age) (phase 2), piglets were fed either the basal diet alone or the basal diet supplemented with *L. reuteri* at a final concentration between $1.1\times10^7$ and $2.3\times10^8$ CFU per ml of diet. Data gathered during this period were analyzed as a randomized complete-block design with four treatments: A—plus *L. reuteri*, not infected with cryptosporidia; B—plus *L. reuteri*, infected with cryptosporidia; C—no *L. reuteri*, not infected with cryptosporidia; and D—no *L. reuteri*, infected with cryptosporidia.

Piglets were weighed daily, and the feed amounts were adjusted according to their weight. Feces consistency or feces/diarrhea scores (1=normal, solid feces; 2=soft, looser than normal stools; and 3=liquid, diarrheal feces) and feed scores (1=eating normally; 2=off feed; 3=not eating; and V=vomiting) were obtained each day for each piglet throughout the entire experimental period.

Rectal swabs were taken at the time when piglets were weighed and they were used for cryptosporidia, hemolytic *E. coli*, and rotavirus assays, as well as for enumeration of *L. reuteri*. The assays for hemolytic *E. coli* and for rotavirus were done to be sure that any diarrhea symptoms were not caused by these common causes of piglet diarrhea. Before placing the rectal swab in a test tube containing 2 ml of PBS (0.01M phosphate buffered saline, pH 7.5), a smear on a glass slide was prepared to determine the presence of cryptosporidia oocysts using the Auramine-O technique (Payne et al., New England J. Med. 309:613–614, 1983). Total lactobacilli and *L. reuteri* enumerations on the swab were carried out by plating decimal dilutions of the phosphate buffered saline (PBS) diluted samples in Lactobacillus-selective agar (LBS)(g/l: trypticase 10; yeast extract 5, $KH_2PO_4$ 61; ammonium citrate 2; sodium acetate (tri-hydrate) 34; $MgSO_4$ (hepta-hydrate) 1.2; $MnSO_4$ (mono-hydrate) 0.13; $FeSO_4$ (hepta-hydrate) 0.06; pH 5.5 adjusted with concentrated HCl) and incubating anaerobically at 37° C. The hemolytic *E. coli* count was determined by streaking swab samples on blood agar plates (Carr Scarborough Microbiologicals, Decatur, Ga.). The presence of rotavirus was assayed on a centrifuged aliquot of the PBS by a latex agglutination technique using the VIROGEN ROTATEST™ kit (Wampole Laboratories, Cranbury, N.J.).

At the end of the experiment, each piglet was sedated and then euthanized. Contents of the ileum and cecum were collected for analysis of total lactobacilli and *L. reuteri*.

Data were subjected to analysis of variance for the comparison of groups according to the experimental designs previously described, and following the General Linear Model (GLM) procedure of SAS (SAS User's Guide: Statistics version 6 edition, SAS Institute, Cary, N.C.). Comparisons of treatment means of data from phase 2 were performed using the Duncan's multiple range test as described in the SAS User's Guide.

Feed scores throughout the entire trial were "1", indicating that the piglets were eating normally.

The feces scores throughout phase 1 varied on the average between 1.0 and 1.4, indicating that most piglets fed either diet A or C had normal feces consistency. With the exception of days 9 and 10 (4 and 5 days after cryptosporidia infection) of phase 2, the average values of feces scores for all other days were similar ($P>0.05$) for all four treatments. The average feces scores for days 9 and 10 were 1.8, 1.4, 1.2, and 1.0 for piglets fed diets D, B, C, and A, and 1.8, 1.4, 1.0 and 1.0 for piglets fed diets D, C, A, and B, respectively. On both days, piglets infected with cryptosporidia and fed the non-supplemented diet D showed more ($P<0.05$) incidence of soft and liquid feces than the other groups. FIG. 1 shows the proportion of piglets which had soft and liquid feces throughout phases 1 and 2. Although the number of piglets per treatment (5) during phase 2 was limited, data shown in FIG. 1 indicate that piglets fed diets C and D (without *L. reuteri*) had a consistent higher incidence of soft and liquid feces than those fed diets A and B.

Shedding scores, in terms of average number of oocysts per field at a magnification of 20× are 1 (5 or fewer oocysts per field); 2 (6–10 oocysts per field); 3 (11–20 oocysts per field) and 4 (greater than 20 oocysts per field). Cryptosporidia oocysts were not detected in feces of piglets which were not infected. Fecal shedding of oocysts was similar ($P>0.05$) for all infected piglets irrespective of the diet fed to them.

The aforementioned data on feces scores and fecal shedding of cryptosporidia oocysts show that infected piglets fed the *L. reuteri*-supplemented diet (B) did not have the diarrhea (soft and/or liquid feces) shown by infected piglets fed the diet without *L. reuteri* (D) demonstrating a protective effect exerted by *L. reuteri* on the sequel of diarrhea that followed cryptosporidia infection.

Quality control of the cow's colostrum and the basal liquid diet showed no lactobacilli, while the levels of *L. reuteri* in the supplemented diet varied between $1.1\times10^7$ and $2.3\times10^8$ CFU per ml. Table 1 presents the results of rectal swabs assayed for *L. reuteri* at days 1, 5, and 12 of the experimental period and shows that piglets fed *L. reuteri* showed larger numbers of this microorganism in the feces than those fed the unsupplemented diet. Thus, there is a correlation between the *L. reuteri* level and the reduction in diarrhea.

TABLE 1

Presence of *L. reuteri*

| Phase-age | Treatment | % Pigs[1] | Range (per swab) |
|---|---|---|---|
| Phase 1 - day 1 | (A): plus *L. reuteri*, non-infected | 60 | $3.0\times10^4$ to $1.2\times10^7$ |
| Phase 1 - day 1 | (C): no *L. reuteri*, non-infected | 30 | $3.0\times10^4$ to $3.7\times10^5$ |
| Phase 1 - day 5 | (A): plus *L. reuteri*, non-infected | 30 | $6.0\times10^6$ to $1.8\times10^8$ |
| Phase 1 - day 5 | (C): no *L. reuteri*, non-infected | 20 | $1.0\times10^4$ |
| Phase 2 - day 12 | (A): plus *L. reuteri*, non-infected | 100 | $8.0\times10^4$ to $6.8\times10^7$ |

TABLE 1-continued

Presence of *L. reuteri*

| Phase-age | Treatment | % Pigs[1] | Range (per swab) |
|---|---|---|---|
| Phase 2 - day 12 | (B): plus *L. reuteri*, cryptosporidia-infected | 80 | $2.5 \times 10^4$ to $1.7 \times 10^7$ |
| Phase 2 - day 12 | (C): no *L. reuteri*, non-infected | 40 | $3.0 \times 10^6$ to $9.5 \times 10^6$ |
| Phase 2 - day 12 | (D): no *L. reuteri*, cryptosporidia-infected | 80 | $3.0 \times 10^4$ to $9.0 \times 10^6$ |

[1]Number of pigs' rectal swabs, expressed as percentage of each group, in which *L. reuteri* was detected.

Table 2 presents the results of total lactobacilli and *L. reuteri* enumerations in the lumen contents of the ileum of piglets, at the end of the experimental period. There was no difference ($P>0.05$) on the total lactobacilli counts; however, the number of *L. reuteri* in the ileum contents of *L. reuteri*-fed piglets was higher than in those fed the non-supplemented diet. Although a similar trend was observed in the cecum contents, the differences among the four treatments were not significant ($P>0.05$).

TABLE 2

| Parameter | A | B | C | D | SEM |
|---|---|---|---|---|---|
| Total Lactobacilli (Log 10 CFU/ml) | 9.48 | 9.66 | 9.39 | 9.20 | 0.38 |
| *L. reuteri* (Log 10 CFU/ml) | 6.87[b] | 6.66[b] | 2.46[a] | 5.75[b] | 1.64 |
| *L. reuteri*/Lactobacilli (ratio Log 10 CFU *L. reuteri*/Lactobacilli × 1000) | 11.46 | 4.22 | 1.87 | 0.21 | — |

[1]Standard error of the mean is the square root of the error mean square.
[a,b]Means in the same row bearing different superscripts differ ($P < 0.05$).

Example II

Studies on humans infected with cryptosporidia also show a significant reduction in symptoms when *L. reuteri* has been administered, including reduced diarrhea (more normal feces/diarrhea scores). For example, immuno-compromised patients, such as those infected with human immunodeficiency virus (HIV) have reduced diarrhea if administered about $10^8$–$10^9$ *L. reuteri* cells per ml in 100 ml/day suspension fluid (water or other fluid consumed by the patient). A preventive effect is seen in patients previously uninfected with cryptosporidia if the patient receive 100 ml/day of a suspension of $10^5$ *L. reuteri* cells.

Example III

*Lactobacillus reuteri* cells for use prophylactically or after infection with cryptosporidia may be suspended in a liquid of choice for direct consumption or further dilution by the patient, for example, in water, fruit juice, milk or another dairy product. Alternatively, the *L. reuteri* cells may be prepared in powder form, in packets, capsules, or other means known in the art for ingestion of dry substances, or may be added to foods.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of reducing symptoms associated with cryptosporda infection in a mammal, comprising administering *Lactobacillus reuteri* cells to the mammal in an amount sufficient to reduce diarrhea in the animal to a level found in control animals not infected with cryptosporidi.

2. The method of claim 1, wherein $10^9$ cells are administered per day until symptoms of cryptosporidia infection are eliminated.

3. The method of claim 1, wherein the cells are administered daily as soon as cryptosporidia infection symptoms are observed.

4. The method of claim 1, wherein the cells are administered prophylactically to a mammal before exposure to cryptosporidia.

5. The method of claim 1, wherein the cells are administered suspended in a liquid.

6. The method of claim 1, wherein the cells are administered in dry form.

7. The method of claim 1, wherein the mammal is a human.

* * * * *